(12) United States Patent
Goi

(10) Patent No.: US 11,167,253 B2
(45) Date of Patent: Nov. 9, 2021

(54) APPARATUS FOR GENERATING ULTRAFINE BUBBLES OF MOLECULAR HYDROGEN IN WATER

(71) Applicant: Lai Huat Goi, Singapore (SG)

(72) Inventor: Lai Huat Goi, Singapore (SG)

(*) Notice: Subject to any disclaimer, the term of this patent is extended or adjusted under 35 U.S.C. 154(b) by 177 days.

(21) Appl. No.: 16/174,896

(22) Filed: Oct. 30, 2018

(65) Prior Publication Data

US 2019/0232238 A1   Aug. 1, 2019

(30) Foreign Application Priority Data

Oct. 30, 2017   (SG) .............................. 10201708891T

(51) Int. Cl.
*B01F 5/04*   (2006.01)
*B01F 3/04*   (2006.01)
(Continued)

(52) U.S. Cl.
CPC .......... *B01F 5/0415* (2013.01); *B01F 3/0446* (2013.01); *B01F 3/04978* (2013.01); *B01F 5/0658* (2013.01); *B01F 5/0665* (2013.01); *B01F 11/0208* (2013.01); *B01F 13/1027* (2013.01); *B01F 2003/04914* (2013.01); *B01F 2215/0032* (2013.01)

(58) Field of Classification Search
CPC .. B01F 3/0446; B01F 3/04978; B01F 5/0415; B01F 5/0658; B01F 5/0665; B01F 11/0208; B01F 13/1027; B01F 2003/04914; B01F 2215/0032
USPC ....................... 261/19, 34.1, 66, 76, DIG. 75
See application file for complete search history.

(56) References Cited

U.S. PATENT DOCUMENTS 5,314,644 A * 5/1994 Michelsen .............. B01F 7/005
  209/170
5,842,600 A * 12/1998 Singleterry ............... A23L 2/54
  222/1
(Continued)

FOREIGN PATENT DOCUMENTS

CN   204502827 U    7/2015
CN   204710217 U   10/2015
(Continued)

OTHER PUBLICATIONS

Intellectual Property Office of Singapore, Written Opinion and Search Report, Application No. SG 10201708891T, dated Jun. 3, 2019.
(Continued)

*Primary Examiner* — Charles S Bushey
(74) *Attorney, Agent, or Firm* — Porter, Wright, Morris & Arthur, LLP

(57) ABSTRACT

An apparatus configured to generate generating water having nano bubbles of molecular hydrogen on demand. The apparatus is connected to a water supply with a valve and has a pump which supplies pressurized water to a venturi gas liquid mixer that also receives a supply of Hydrogen gas. The mixed hydrogen gas/water steam is provided to a nano bubble generating apparatus that uses cavitation to generate nano bubbles of Hydrogen in the water. The Hydrogen nano bubbles have diameters of less than 200 nm and a concentration of up to 1.2 ppm. Further the concentration remains with 85% of the output concentration for at least 12 hours.

21 Claims, 2 Drawing Sheets

(51) Int. Cl.
   *B01F 11/02* (2006.01)
   *B01F 13/10* (2006.01)
   *B01F 5/06* (2006.01)

(56) References Cited

U.S. PATENT DOCUMENTS

| | | | | |
|---|---|---|---|---|
| 5,938,982 | A * | 8/1999 | Sugiura | B01F 5/0659 |
| | | | | 261/75 |
| 7,624,969 | B2 * | 12/2009 | Schletz | B01F 5/0057 |
| | | | | 261/36.1 |
| 7,913,984 | B2 * | 3/2011 | Noguchi | B01F 3/0446 |
| | | | | 261/29 |
| 8,038,127 | B2 * | 10/2011 | Matsuoka | B01F 5/0691 |
| | | | | 261/21 |
| 8,186,653 | B2 * | 5/2012 | Tsuji | B01F 3/0446 |
| | | | | 261/79.2 |
| 9,061,255 | B2 * | 6/2015 | Song | B01F 5/0696 |
| 2004/0251566 | A1 * | 12/2004 | Kozyuk | B01F 5/0646 |
| | | | | 261/76 |
| 2005/0077636 | A1 * | 4/2005 | Bortkevitch | B01F 5/0428 |
| | | | | 261/76 |
| 2007/0257381 | A1 * | 11/2007 | Chuang | B01F 5/12 |
| | | | | 261/76 |
| 2015/0273408 | A1 * | 10/2015 | Tachibana | B01F 15/00538 |
| | | | | 366/162.4 |
| 2017/0216794 | A1 * | 8/2017 | Kamimura | B01F 15/0243 |

FOREIGN PATENT DOCUMENTS

| | | |
|---|---|---|
| CN | 205084639 U | 3/2016 |
| JP | 2007021343 A | 2/2007 |
| JP | 2014076425 A | 5/2014 |
| JP | 2015188857 A | 11/2015 |
| JP | 2016043347 A | 4/2016 |
| JP | 2017031129 A | 2/2017 |
| JP | 2017196612 A | 11/2017 |
| WO | 2014204399 A1 | 12/2014 |

OTHER PUBLICATIONS

UK Intellectual Property Office, Search Report, Application No. GB 1817709.7, dated Apr. 30, 2019.

* cited by examiner

APPARATUS FOR GENERATING ULTRAFINE BUBBLES OF MOLECULAR HYDROGEN IN WATER

TECHNICAL FIELD

The present disclosure relates generally to an apparatus for generating ultrafine bubbles of molecular hydrogen in water. In a particular form the present disclosure relates to apparatus for dispensing hydrogen drinking water in which hydrogen stays dissolved for long periods of time.

BACKGROUND

Since a 2007 Nature Medicine paper from the laboratory of Dr. Ohta Shigeo (Ohsawa et al, Nature Medicine 13, 688-694 (2007), doi:10.1038/nm1577) found that molecular Hydrogen ($H_2$) acts as a therapeutic antioxidant by selectively reducing cytotoxic oxygen radicals, considerable interest has been generated for the use of Hydrogen water, that is, water containing dissolved molecular hydrogen ($H_2$), for therapeutic applications in the health care and medical industries. Further basic and clinical research has suggested that Hydrogen water is an important physiological regulatory factor producing antioxidant and anti-inflammatory effects on cells and organs, and it is believed to be effective in preventing or mitigating lifestyle-related diseases.

To increase uptake and thus potential therapeutic benefit, it would be desirable to be able to produce hydrogen bubble water at room temperature and on demand for supply by taps or water dispensers for immediate or later consumption (eg over the next day). However generating hydrogen water on demand has some difficulties as the solubility of hydrogen in water is low, and hydrogen does not stay dissolved in water for extended periods of time. Whilst some methods for generating hydrogen water have been developed, these suffer from a number of issues.

For example, US20120087990A1 proposes contacting water containing one or both of calcium ions and magnesium ions with a metal (eg Magnesium) or metal oxide hydrogen molecule dissociative adsorption catalyst to increase the concentration of active hydrogen in the water. However this requires pre-treatment of the water, frequent replacement of the metal catalyst, and leaves the water with additional additives. US20130043124A1 uses a proton exchange membrane (PEM) with direct current power to the electrolytic cell. The PEM electrolytic cell system requires complicated elements to generate hydrogen water, leading to high maintenance costs and frequent servicing, and leaves additional additives in the water. US20170065940A1 describes a recirculation system in which electrolysis is used to generate Hydrogen gas, and this is dissolved in water under pressure using a diaphragm pump. However this system requires continuous recirculation of water to increase and maintain the dissolved Hydrogen. Other physical methods comprise mixing of Hydrogen gas and liquid using turbulent flows to dissolve Hydrogen or using pressurized dissolution where a gas is forcibly dissolved into liquid using a compressor, ultrasonic or impulse waves to create cavitation and formation of hydrogen bubbles. However due to low solubility of Hydrogen in water these arrangements are often complex and the Hydrogen does not stay dissolved in water for long periods (ie hours).

There is thus a need to provide a simple apparatus for generating ultrafine molecular hydrogen that stays dissolved in water for many hours or at least provide a useful alternative to existing apparatus.

SUMMARY

According to a first aspect, there is provided an apparatus configured to generate water comprising nano bubbles of molecular hydrogen comprising:

an input connector which in use is connected to a water source;

a valve for controlling a flow of water into the apparatus via the input connector;

a venturi gas-liquid mixer downstream of the valve and configured to receive a flow of pressurised water when the valve is open and a flow of Hydrogen gas from a hydrogen gas source, wherein the gas water mixer apparatus generates a mixed hydrogen gas/water output stream;

a nano bubble generating apparatus which receives the mixed hydrogen gas/water stream connected to the output of the venturi mixer and generates Hydrogen nano bubbles using a cavitation mechanism, wherein the nano bubble generating apparatus produces an output hydrogen water steam comprising Hydrogen nano bubbles with diameters of less than 200 nm at an output concentration of between 0.8 and 1.2 ppm wherein the concentration remains with 85% of the output concentration for at least 12 hours.

In one form, the concentration remains within 85% of the output concentration for at least 15 hours, and/or within 63% of the output concentration for at least 18 hours, and/or within 50% of the output concentration for at least 20 hours, and/or within 37% of the output concentration for at least 24 hours.

In one form, the apparatus further comprises a pump connected between the valve and the venturi gas-liquid mixer to pressurise the output water to at least one bar. In one form the pump pressurises the output water to be between one and three bar. In one form the pump has a rating of less than 100 W.

In one form, the venturi gas-liquid mixer generates a mixed hydrogen gas/water output stream with a speed of between 0.5-1.5 m/s and a flow rate of between 1.5-2.5 l1 min.

In one form, the hydrogen gas source is a gas bottle containing Hydrogen gas and a regulator.

In one form, the apparatus further comprises a housing and the gas bottle, pump if present, venturi gas-liquid mixer and nano bubble generating apparatus are contained in the housing, and the housing has dimensions of 400 mm×450 mm×200 mm or less.

In one form, the apparatus further comprises a housing and the pump if present, venturi gas-liquid mixer and nano bubble generating apparatus are contained in the housing, and the gas bottle is external to the housing and supplied regulated hydrogen gas to the apparatus via a regulated connection.

In one form, the apparatus further comprises a temperature control apparatus located prior to the venturi gas-liquid mixer to reduce or increase the temperature of the water provided to the venturi gas-liquid mixer.

According to a second aspect, there is provided a method for generating water comprising nano bubbles of molecular hydrogen comprising:

receiving an input flow of water with a pressure of at least one bar;

receiving an input flow of Hydrogen gas;

mixing the input flow of water with the input flow of Hydrogen gas in a venturi gas-liquid mixer to generates a mixed hydrogen gas/water output stream;

generating Hydrogen nano bubbles using a cavitation mechanism in a nano bubble generating apparatus which receives the mixed hydrogen gas/water stream and produces an output hydrogen water steam comprising Hydrogen nano bubbles with diameters of less than 200 nm at an output concentration of between 0.8 and 1.2 ppm wherein the concentration remains with 85% of the output concentration for at least 12 hours.

In one form, the concentration remains within 85% of the output concentration for at least 15 hours, and/or within 63% of the output concentration for at least 18 hours, and/or within 50% of the output concentration for at least 20 hours, and/or within 37% of the output concentration for at least 24 hours.

In one form, the input water has a pressure of between one and three bar and is provided by a pump connected to a water supply.

In one form, the venturi gas-liquid mixer generates a mixed hydrogen gas/water output stream with a speed of between 0.5-1.5 m/s and a flow rate of between 1.5-2.5 L/min.

BRIEF DESCRIPTION OF DRAWINGS

Embodiments of the present disclosure will be discussed with reference to the accompanying drawings wherein.

In the following description, like reference characters designate like or corresponding parts throughout the figures.

DESCRIPTION OF EMBODIMENTS

Figure 1:
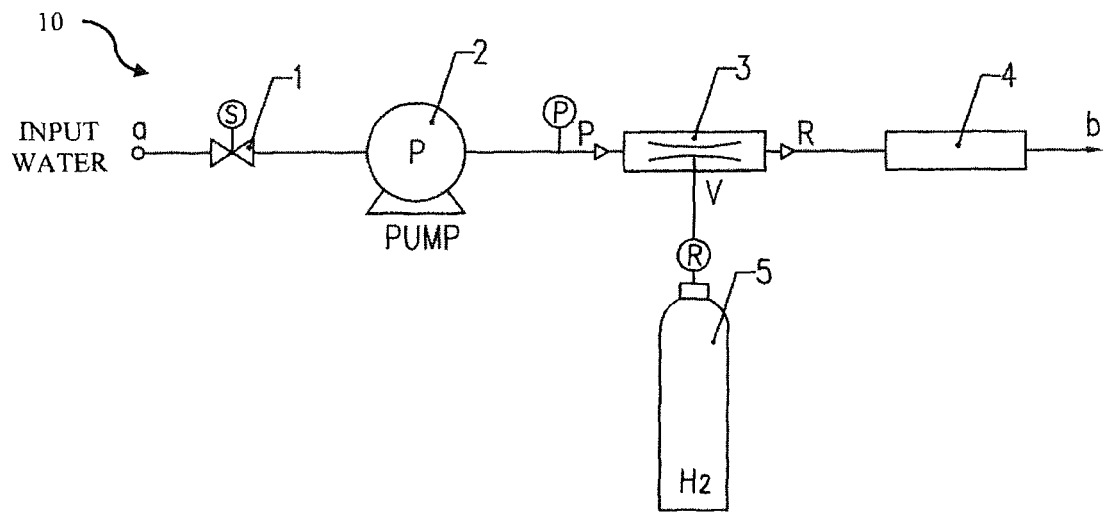
FIG. 1 is a schematic diagram of an apparatus 10 configured to generate water containing ultrafine bubbles of molecular hydrogen according to an embodiment.

Referring now to FIG. 1, there is shown an apparatus 10 configured to generate water containing ultrafine bubbles of molecular hydrogen. Input or raw (eg tap or supply water) water is supplied at input connection (a) to a user control valve (1) which is opened by a user to supply water to a booster pump (2) and subsequent components. The booster pump (2) generates a high pressure water stream at outlet (P) which is supplied to a Venturi gas-liquid mixing device (3) at a Venturi mixer inlet connection. In one embodiment the booster pump pressurizes the water to at least 1 bar. In one embodiment the booster pump is a small pump with a rating of less than 100 watts and generates pressures in the range 1-3 bar. The Venturi gas-liquid mixing device (3) also receives a supply of molecular Hydrogen $H_2$ gas (5) from a supply source, which in this embodiment is a pressurized gas bottle with regulator (R) and generates a flow rate of 0.8-1.5 L/min.

The Venturi gas-liquid mixing device (3) mixes the hydrogen gas and water (using the Venturi effect) to deliver a high speed low flow rate mixed hydrogen gas/water stream to the input connection of a nano bubble generating apparatus (4). In one embodiment, the output hydrogen gas/water jet has a (high) speed of around 0.5-1.5 m/s, and a (low) flow rate of 1.5-2.5 L/min.

The nano bubble generating apparatus spins the input hydrogen gas/water through the apparatus and uses cavitation to dissolve the Hydrogen as nano bubbles in the water, generates an output stream of water containing ultrafine nano bubbles of molecular hydrogen at output (b). The apparatus can be used to generate hydrogen water at normal (one) atmospheric pressure and room temperature (25 degree Celsius) in which molecular hydrogen ($H_2$) has a concentration of up to 1.2 ppm and stays dissolved for long periods of time.

Figure 2A:
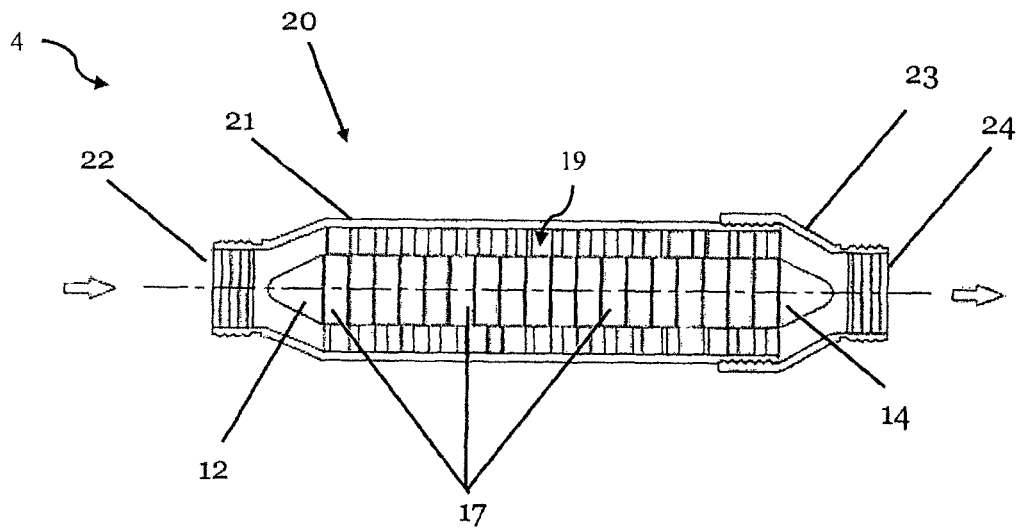
FIG. 2A is a cross sectional view of an embodiment of a nano bubble generating apparatus according to an embodiment.
Figure 2B:
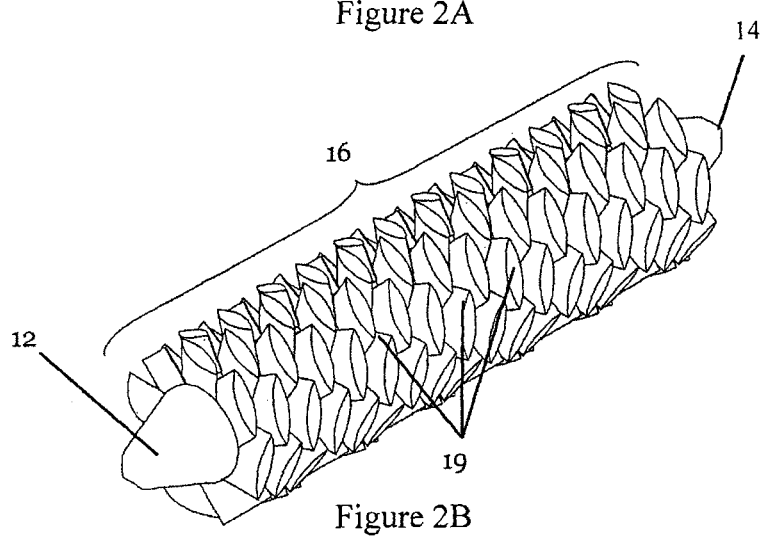
FIG. 2B is a perspective view of the cylindrical body with the air-foil shaped projecting members housed within the tubular member of a nano bubble generating apparatus according to an embodiment.

In one embodiment, the nano bubble generating apparatus 4 is an embodiment of an apparatus as described in WO2014204399 titled AN APPARATUS FOR GENERATING NANOBUBBLES. This apparatus 4 comprises a tubular member 20 containing a longitudinal shaft having a cylindrical body 16, and first 12 and second end 14 portions formed as conical-shaped guides. The conical-shaped guide streamlines fluid flow from the venturi guide at the input 22 and to a fluid dispensing fitting at the output 24. The cylindrical body includes air-foil shaped projecting members 19 which protrude radially from the longitudinal shaft formed from a plurality of discs 17. The air-foil shaped projecting members are arranged in a predetermined manner on the outer circumferential surface of the disc member such that the projecting members do not overlap each other, leaving a slight gap in between each projecting member. The tubular member is formed as a cylindrical housing 21 which connects to an end piece 23. The diameter of the shaft and projecting members is slightly less than the inner diameter of the tubular member 20 to keep the fluid flow within the tubular member 20 in close contact with the airfoil-shaped projecting members 19. FIG. 2A is a cross sectional view of an embodiment of the nano bubble generating apparatus 4 and FIG. 2B is a perspective view of the cylindrical body 16 with the air-foil shaped projecting members 19 housed within the tubular member 20, having 22 mm diameter by 180 mm in length.

When the mixed hydrogen gas and water flows through the fluid supply inlet 22 of the tubular member 20 (eg from the Venturi mixer 3) it is guided by the conical-shaped guide 12 proximal to the inlet of the longitudinal shaft 22 and fed into the airfoil-shaped projecting members 19 of the body 16. When the fluid flow passes through the flow passage between two airfoil-shaped projecting members 19, the fluid converges and experiences a Venturi effect in that the velocity of the fluid flow increases as it passes through the airfoil-shaped projecting members 19. As fluid flow leaves the flow passage, it encounters a divergent flow from another airfoil-shaped projecting member 19 in its path which splits the fluid flow through the subsequent flow passages. The repeated convergent and divergent flow of fluid through the multiple flow passages causes velocity and pressure fluctuation and accelerates the formation of vortexes known as the Coanda effect. This causes the cavitation of nano bubbles of Hydrogen gas from the fierce whirl created from the fluid flow through the multiple flow passages. The fluid flow swirls through the flow passages and is guided by the conical shaped guide 14 at the outlet 24 of the tubular member. The fluid flow that exits the tubular member 20 will contain numerous nano bubbles.

Figure 3:
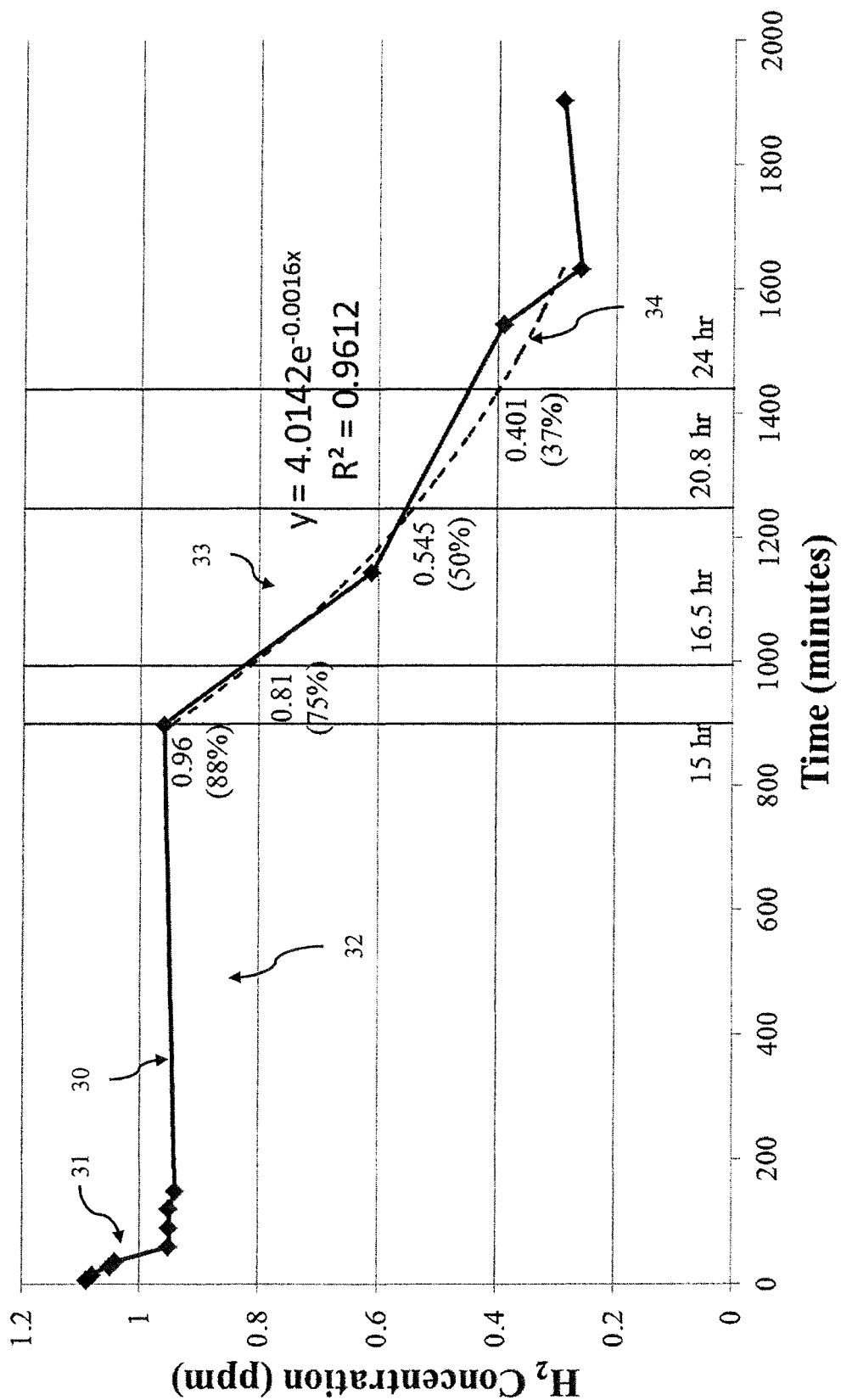
FIG. 3 is a graph of the concentration of dissolved Hydrogen nano bubbles as a function of time generated from an embodiment of an apparatus configured to generate water containing ultrafine bubbles of molecular hydrogen.

When the nano bubble generating apparatus 4 is combined with components described previously, highly concentrated ultrafine bubbles of molecular hydrogen can be dissolved in room temperature water at concentrations of up to 1.2 ppm. Further the ultrafine hydrogen bubbles stay dissolved in the hydrogen water for long periods of time. An embodiment of the apparatus was used to generate a sample of hydrogen bubble water which was left exposed at room temperature, and the concentration of Hydrogen was repeatedly measured over a 32 hour period. Table 1 below is a plot of the measured concentration as a function of time, and FIG. 3 is a plot of the concentration 30 of molecular Hydrogen ($H_2$) as a function of time in minutes.

TABLE 1

Measured Concentration of $H_2$ nano bubbles in a sample of Hydrogen water as a function of time.

| $H_2$ Concentration (PPM) | Relative Concentration (with respect to $t_0$) | Elapsed Time In Minutes | Elapsed Time In Hours |
|---|---|---|---|
| 1.09 | 100% | 0 | 0.0 |
| 1.09 | 100% | 6 | 0.1 |
| 1.08 | 99% | 15 | 0.3 |
| 1.05 | 96% | 28 | 0.5 |
| 1.04 | 95% | 36 | 0.6 |
| 0.95 | 87% | 60 | 1.0 |
| 0.95 | 87% | 90 | 1.5 |
| 0.95 | 87% | 120 | 2.0 |
| 0.94 | 86% | 150 | 2.5 |
| 0.96 | 88% | 900 | 15.0 |
| 0.61 | 56% | 1145 | 19.1 |
| 0.39 | 36% | 1545 | 25.8 |
| 0.26 | 24% | 1635 | 27.3 |
| 0.29 | 27% | 1905 | 31.8 |

As can be seen from Table 1 and FIG. 3, the initial concentration of molecular hydrogen was 1.09 ppm (with bubble diameters of 200 nm or smaller). It can be seen from the first portion 31 of concentration curve 30 that there was a roughly a linear decrease in concentration over the first 60 minutes from 1.09 ppm to 0.95 ppm—a 13% reduction to a relative concentration of 87%. In the second portion 32 of the concentration curve 30 from 1 hour to 15 hours (60 minutes to 900 m), the concentration remained extremely stable with no detectable decrease (within measurement errors). That is for 14 hours there was no detected change in concentration and for the first 15 hours (900 minutes) the concentration was always greater than 85% of the initial concentration ie greater than 0.927 ppm for first 15 hours after generation.

In the third portion 33 of the concentration curve (after 15 hours) the concentration underwent an approximately exponential decay before flattening out around 1600 minutes (~27 hours). To model this decay an exponential decay curve was fitted to data from 900 minutes (15 hours) until 1635 minutes (27.3 hours):

$$y = 4.0142 e^{-0.0016 t} \{t: 900 < t < 1635\} \quad \text{Equation 1}$$

The $R^2$ value for the fit was 0.961 indicating an extremely high (good) correlation coefficient of 98%. Equation 1 can inverted and used to estimate threshold values (and the time constant), and Table 2 below lists estimates for concentration reductions of 75%, 63% (1−1/e), 50%, 37% (1/e) and 25% (in both minutes and hours). Dashed line 34 plots the exponential fit according to equation 1 over the third portion 33 and closely follows the data points in this range (and piecewise linear curve 30), consistent with the high correlation coefficient.

TABLE 2

Estimated Concentration of $H_2$ as a function of time since addition according to Equation 1.

| $H_2$ Concentration (PPM) | Concentration Reduction | Elapsed Time In Minutes | Elapsed Time In Hours |
|---|---|---|---|
| 0.818 | 75% | 995 | 16.6 |
| 0.689 | 63% | 1101 | 18.4 |
| 0.545 | 50% | 1248 | 20.8 |
| 0.401 | 37% | 1440 | 24.0 |
| 0.273 | 25% | 1681 | 28.0 |

The time constant of this decay is thus given by the 37% (or 1/e) value which is 24 hours (1440 minutes). The data was also well described by a linear fit with an $R^2$ value of 0.958 (y=−0.0008699t+1.69126), although this tended to extend the elapsed time values by up to 5% during the decay region (for example the linear estimates of 75%, 63%, 50% were 16.7, 19.2, and 22 hours respectively).

Embodiments of the apparatus operate at under one atmospheric pressure and at room temperature of 25 degree Celsius and generates hydrogen bubble water with concentration of 0.9-1.2 ppm and with bubble diameters of 200 nm or smaller. Embodiments of the apparatus can be connected to a standard water supply and water supply valve (eg a tap) 1 can be operated by a user to allow water to flow through the apparatus and generate hydrogen water containing ultrafine bubbles of molecular Hydrogen on demand. Embodiments of the apparatus are relatively simple and compact and can be located within a housing or in cupboard near a tap, and can be installed at a home or in a workplace within 600 mm×500 mm×300 mm. In one embodiment the housing has dimensions of 400 mm×450 mm×200 mm or less. In one embodiment the hydrogen gas bottle 5 is included in a housing with the other components. In another embodiment, the hydrogen gas bottle 5 could be stored remotely of the housing, such as in an external of a building containing the housing, and gas supplied via a gas supply line.

Other variations of the apparatus are possible. For example a temperature control apparatus could be included to chill the water. In this embodiment the input water is passed through a coil in contact with a heat exchanger and coolant under control of a microcontroller or electronic control circuit. Preferably the temperature control apparatus is located prior (upstream) of the Venturi mixer 3 so that the water is at a desired temperature prior to contact with the hydrogen gas. In this way a chilled hydrogen water dispenser could be provided in a home or a workplace. In another embodiment, the heat exchanger could be used to heat the water (replacing the coolant with heating elements). In another embodiment the pump (2) could be omitted if water is supplied via connector (a) at an appropriate pressure of not less than 3 bars for the venturi mixer.

In another embodiment the hydrogen gas bottle 5 could be replaced with an alternate Hydrogen source, such as a supply line from an external source or reservoir, or alternatively a hydrogen gas generating apparatus could provide hydrogen gas as required. For example the hydrogen gas generating apparatus could be electrolysis based device with a reservoir and pump which generates and supplies hydrogen gas.

In another embodiment the venturi water-gas mixer could be replaced with an alternative water-gas mixing apparatus which can supply a water gas stream to the nano bubble generating apparatus at a suitable pressure and rate, such as around 0.5 m/s and a flow rate of 1.5 L/min.

In another embodiment, the nano bubble generating device could be modified from that described in WO2014204399, provided it was capable of generating hydrogen nano bubbles with diameters of less than 200 nm from an input mixed hydrogen/water stream.

The apparatus generates ultrafine bubble molecular hydrogen water on demand directly from normal water, with concentrations of up to 1.2 ppm achievable. Further the ultrafine bubbles of molecular hydrogen stay dissolved in water for comparatively long periods of time compared to prior art systems. This allows a cup or flask to be filled and then drunk over the next half day (12 hours) with only a small reduction in concentration (less than 15%). Further even if consumed 24 hours after dispensing the concentration remains at 37% (0.4 ppm). Additionally the apparatus is of simple construction and generates Hydrogen water without changing the characteristics of the original drinking water.

Throughout the specification and the claims that follow, unless the context requires otherwise, the words "comprise" and "include" and variations such as "comprising" and "including" will be understood to imply the inclusion of a stated integer or group of integers, but not the exclusion of any other integer or group of integers.

The reference to any prior art in this specification is not, and should not be taken as, an acknowledgement of any form of suggestion that such prior art forms part of the common general knowledge.

It will be appreciated by those skilled in the art that the disclosure is not restricted in its use to the particular application or applications described. Neither is the present disclosure restricted in its preferred embodiment with regard to the particular elements and/or features described or depicted herein. It will be appreciated that the disclosure is not limited to the embodiment or embodiments disclosed, but is capable of numerous rearrangements, modifications and substitutions without departing from the scope as set forth and defined by the following claims.

The invention claimed is:

1. An apparatus configured to generate water comprising nano bubbles of molecular hydrogen comprising:
   an input connector which in use is connected to a water source;
   a valve for controlling a flow of water into the apparatus via the input connector;
   a venturi gas-liquid mixer downstream of the valve and configured to receive a flow of pressurised water when the valve is open and a flow of Hydrogen gas from a hydrogen gas source, wherein the gas water mixer apparatus generates a mixed hydrogen gas/water output stream; and
   a nano bubble generating apparatus which receives the mixed hydrogen gas/water stream connected to the output of the venturi mixer such that Hydrogen nano bubbles are generated using a cavitation mechanism, wherein the nano bubble generating apparatus is configured to produce an output hydrogen water steam comprising Hydrogen nano bubbles with diameters of less than 200 nm at an output concentration of between 0.8 and 1.2 ppm wherein the concentration remains within 85% of the output concentration for at least 12 hours.

2. The apparatus as claimed in claim 1, wherein the nano bubble generating apparatus is configured so that the concentration remains within 85% of the output concentration for at least 15 hours.

3. The apparatus as claimed in claim 1, wherein the nano bubble generating apparatus is configured so that the concentration remains within 63% of the output concentration for at least 18 hours.

4. The apparatus as claimed in claim 1, wherein the nano bubble generating machine is configured so that the concentration remains within 50% of the output concentration for at least 20 hours.

5. The apparatus as claimed in claim 1, wherein the nano bubble generating machine is configured so that the concentration remains within 37% of the output concentration for at least 24 hours.

6. The apparatus as claimed in claim 1, further comprising a pump connected between the valve and the venturi gas-liquid mixer to pressurise the output water to at least one bar.

7. The apparatus as claimed in claim 6, wherein the pump is configured to pressurise the output water to be between one and three bar.

8. The apparatus as claimed in claim 6, wherein the pump has a rating of less than 100 W.

9. The apparatus as claimed in claim 1, wherein the venturi gas-liquid mixer is configured to generate mixed hydrogen gas/water output stream with a speed of between 0.5-1.5 m/s and a flow rate of between 1.5-2.5 L/min.

10. The apparatus as claimed in claim 1, wherein the hydrogen gas source is a gas bottle containing Hydrogen gas and a regulator.

11. The apparatus as claimed in claim 10, wherein the apparatus further comprises a housing and the gas bottle, pump if present, venturi gas-liquid mixer and nano bubble generating apparatus are contained in the housing, and the housing has dimensions of 400 mm×450 mm×200 mm or less.

12. The apparatus as claimed in claim 10, wherein the apparatus further comprises a housing and the pump if present, venturi gas-liquid mixer and nano bubble generating apparatus are contained in the housing, and the gas bottle is external to the housing and supplied regulated hydrogen gas to the apparatus via a regulated connection.

13. The apparatus as claimed in claim 1, further comprising a temperature control apparatus located prior to the venturi gas-liquid mixer to reduce or increase the temperature of the water provided to the venturi gas-liquid mixer.

14. The apparatus as claimed in claim 1, wherein the nano bubble generating apparatus comprises:
   a core member having an inlet and an outlet defining a flow path for the mixed hydrogen gas/water stream; and
   a plurality of projections extending radially from the core member;
   wherein when the mixed hydrogen gas/water stream flows along the flow path, the mixed hydrogen gas/water stream is fed through a flow passage between two projections with increased velocity and collides with the mixed hydrogen gas/water stream from another flow passage such that Hydrogen nano bubbles are generated.

15. A method for generating water comprising nano bubbles of molecular hydrogen comprising:
   receiving an input flow of water with a pressure of at least one bar;
   receiving an input flow of Hydrogen gas;
   mixing the input flow of water with the input flow of Hydrogen gas in a venturi gas-liquid mixer to generate a mixed hydrogen gas/water output stream;
   generating Hydrogen nano bubbles using a cavitation mechanism in a nano bubble generating apparatus which receives the mixed hydrogen gas/water stream into the nano bubble generating apparatus and producing with the nano bubble generating apparatus an output hydrogen water steam comprising Hydrogen nano bubbles with diameters of less than 200 nm at an output concentration of between 0.8 and 1.2 ppm wherein the concentration remains within 85% of the output concentration for at least 12 hours.

16. The method as claimed in claim 15, wherein the step of generating hydrogen nano bubbles comprises the step of producing with the nano bubble generating apparatus an output Hydrogen water stream comprising Hydrogen nano bubbles with diameters of less than 200 nm at an output concentration of between 0.8 and 1.2 ppm wherein the concentration remains within 85% of the output concentration for at least 15 hours.

17. The method as claimed in claim 15 wherein the step of generating Hydrogen nano bubbles comprises the step of producing with the nano bubble generating apparatus an output Hydrogen water stream comprising Hydrogen nano bubbles with diameters of less than 200 nm at an output concentration of between 0.8 and 1.2 ppm wherein the concentration remains within 63% of the output concentration for at least 18 hours.

18. The method as claimed in claim 15 wherein the step of generating Hydrogen nano bubbles comprises the step of producing with the nano bubble generating apparatus an output Hydrogen water stream comprising Hydrogen nano bubbles with diameters of less than 200 nm at an output concentration of between 0.8 and 1.2 ppm wherein the concentration remains within 50% of the output concentration for at least 20 hours.

19. The method as claimed in claim 15 wherein the step of generating Hydrogen nano bubbles comprises the step of producing with the nano bubble generating apparatus an output Hydrogen water stream comprising Hydrogen nano bubbles with diameters of less than 200 nm at an output concentration of between 0.8 and 1.2 ppm wherein the concentration remains within 37% of the output concentration for at least 24 hours.

20. The method as claimed in claim 15 wherein input water has a pressure of between one and three bar and is provided by a pump connected to a water supply.

21. The method as claimed in claim 15 wherein the venturi gas-liquid mixer generates a mixed hydrogen gas/water output stream with a speed of between 0.5-1.5 m/s and a flow rate of between 1.5-2.5 L/min.

* * * * *